(12) United States Patent
Katsevich

(10) Patent No.: US 7,010,079 B2
(45) Date of Patent: Mar. 7, 2006

(54) 3PI ALGORITHM FOR SPIRAL CT

(75) Inventor: Alexander Katsevich, Oviedo, FL (US)

(73) Assignee: Research Foundation of the University of Central Florida, Orlando, FL (US)

(*) Notice: Subject to any disclaimer, the term of this patent is extended or adjusted under 35 U.S.C. 154(b) by 267 days.

(21) Appl. No.: 10/728,136

(22) Filed: Dec. 4, 2003

(65) Prior Publication Data

US 2004/0125910 A1 Jul. 1, 2004

Related U.S. Application Data

(63) Continuation-in-part of application No. 10/389,534, filed on Mar. 14, 2003, now Pat. No. 6,804,321, which is a continuation-in-part of application No. 10/389,090, filed on Mar. 14, 2003, now Pat. No. 6,771,733, which is a continuation-in-part of application No. 10/143,160, filed on May 10, 2002, now Pat. No. 6,574,299.

(60) Provisional application No. 60/430,802, filed on Dec. 4, 2002, provisional application No. 60/312,827, filed on Aug. 16, 2001.

(51) Int. Cl.
A61B 6/03 (2006.01)

(52) U.S. Cl. .............................. 378/4; 378/15; 378/901
(58) Field of Classification Search .................... 378/4, 378/8, 15, 19, 901
See application file for complete search history.

(56) References Cited

U.S. PATENT DOCUMENTS 6,898,264 B1 * 5/2005 Katsevich ...................... 378/4
2004/0223581 A1 * 11/2004 Katsevich ...................... 378/4

FOREIGN PATENT DOCUMENTS

WO WO 2004084137 A2 * 9/2004

* cited by examiner

Primary Examiner—David V Bruce
(74) Attorney, Agent, or Firm—Brian S. Steinberger; Law Offices of Brian S. Steinberger, P.A.

(57) ABSTRACT

Methods and systems for reconstructing images of moving objects being spirally scanned with two dimensional detectors with a 3PI algorithm. The moving objects can be scanned at a rate of up to approximately three times slower than those of pre-existing systems. In a preferred embodiment, the invention allows for a patient on a table moving through a spiral scanner to be slowed down by a factor of up to three, and still use the same size detector array as those in existing spiral scanning systems.

25 Claims, 14 Drawing Sheets

Overview of the basic process steps of the invention

Fig. 18

Step 20. Finding families of lines for filtering

Step 21. From the family of lines $\mathcal{L}_0$ choose an equidistant set of lines that are parallel to the spiral tangent and that cover the projection of the region of interest onto the detector plane located between $\Gamma_2$ and $\Gamma_{-2}$ (see Fig. 11).

Step 22. From the family of lines $\mathcal{L}_1$ choose a discrete set of lines that are tangent to $\Gamma_1$ and $\Gamma_{-1}$ (see Fig. 12). The extreme left point of tangency on $\Gamma_1$ should coincide with the point where the double tangent line $\mathcal{L}_{-1,1}^{cr}$ is tangent to $\Gamma_1$. Similarly, the extreme right point of tangency on $\Gamma_{-1}$ should coincide with the point where the double tangent line $\mathcal{L}_{-1,1}^{cr}$ is tangent to $\Gamma_{-1}$.

Step 23. From the family of lines $\mathcal{L}_2$ choose a discrete set of lines that are tangent to $\Gamma_2$ and $\Gamma_{-2}$ (see Fig. 14, left panel). In both cases the points of tangency do not have to extend beyond the projection of the region of interest onto the detector plane. In case of the improved algorithm, instead of the lines tangent to $\Gamma_2$ and $\Gamma_{-2}$, we choose a discrete (say, equidistant) set of values for $s_3$ on the curves $\Gamma_2$ and $\Gamma_{-2}$ and then determine the lines $L \in \mathcal{L}_2'$ by solving equations (21), (22). On both curves the points $s_3$ do not have to extend beyond the projection of the region of interest onto the detector plane.

Step 30

3PI ALGORITHM FOR SPIRAL CT

This invention claims the benefit of priority to U.S. Provisional Application Ser. No. 60/430,802 filed, Dec. 4, 2002, and is a Continuation-In-Part of U.S. patent application Ser. No. 10/389,534 filed Mar. 14, 2003, now U.S. Pat. No. 6,804,321, which is a Continuation-In-Part of Ser. No. 10/389,090 filed Mar. 14, 2003, now U.S. Pat. No. 6,771,733, which is a Continuation-In-Part of Ser. No. 10/143,160 filed May 10, 2002 now U.S. Pat. No. 6,574,299, which claims the benefit of priority to U.S. Provisional Application 60/312,827 filed Aug. 16, 2001.

FIELD OF INVENTION

This invention relates to computer tomography, and in particular to processes, methods and systems for reconstructing three-dimensional images from the data obtained by spiral scans using 3PI algorithm.

BACKGROUND AND PRIOR ART

Over the last thirty years, computer tomography (CT) has gone from image reconstruction based on scanning in a slice-by-slice process to spiral scanning. From the 1970s to 1980s the slice-by-slice scanning was used. In this mode the incremental motions of the patient on the table through the gantry and the gantry rotations were performed one after another. Since the patient was stationary during the gantry rotations, the trajectory of the x-ray source around the patient was circular. Pre-selected slices through the patient have been reconstructed using the data obtained by such circular scans. From the mid 1980s to present day, spiral type scanning has become the preferred process for data collection in CT. Under spiral scanning a table with the patient continuously moves through the gantry that is continuously rotating about the table. At first, spiral scanning has used one-dimensional detectors, which receive data in one dimension (a single row of detectors). Later, two-dimensional detectors, where multiple rows (two or more rows) of detectors sit next to one another, have been introduced. In CT there have been significant problems for image reconstruction especially for two-dimensional detectors. In what follows the data provided by the two-dimensional detectors will be referred to as cone-beam (CB) data or CB projections.

For three-dimensional (also known as volumetric) image reconstruction from the data provided by a spiral scan with two-dimensional detectors, there are two known groups of algorithms: Exact algorithms and Approximate algorithms, that each have known problems. Under ideal circumstances, exact algorithms can provide a replication of an exact image. Thus, one should expect that exact algorithms would produce images of good quality even under non-ideal (that is, realistic) circumstances. However, exact algorithms can be known to take many hours to provide an image reconstruction, and can take up great amounts of computer power when being used. These algorithms can require keeping considerable amounts of cone beam projections in memory. Additionally, some exact algorithms can require large detector arrays to be operable and can have limits on the size of the patient being scanned.

Approximate algorithms possess a filtered back projection (FBP) structure, so they can produce an image very efficiently and using less computing power than Exact algorithms. However, even under the ideal circumstances they produce an approximate image that may be similar to but still different from the exact image. In particular, Approximate algorithms can create artifacts, which are false features in an image. Under certain circumstances these artifacts could be quite severe.

The first group of algorithms that are theoretically exact and have the shift-invariant FBP structure was disclosed in U.S. patent application Ser. No. 10/143,160 filed May 10, 2002, now U.S. Pat. No. 6,574,299, which claims the benefit of priority to U.S. Provisional Application 60/312,827 filed Aug. 16, 2001. A shortcoming of these algorithms is that they operate in the 1PI mode. This means that if the detector array is large in the axial direction, then one has to translate the patient through the gantry very quickly in order to use all of the detector. However, rapid motion of the patient is very impractical for obvious reasons. On the other hand, if the patient moves slowly, only part of the detector is used. This leads to undesirable consequences: part of the x-ray dose is wasted, discretization artifacts are enhanced, noise stability is reduced, etc.

SUMMARY OF THE INVENTION

A primary objective of the invention is to provide 3PI algorithms for reconstructing images of objects that have been scanned in a spiral fashion with two-dimensional detectors. For image reconstruction at any given voxel these algorithms require a longer section of the spiral than the 1PI algorithms of U.S. patent application Ser. No. 10/143,160 filed May 10, 2002, now U.S. Pat. No. 6,574,299, which is incorporated by reference, which claims the benefit of priority to U.S. Provisional Application 60/312,827 filed Aug. 16, 2001. Consequently, the new algorithms allow to slow the patient down by about a factor of three, but still use the same size detector array.

A first preferred embodiment of the invention uses a five overall step process for reconstructing the image of an object under a spiral scan. In a first step a current CB projection is measured. Next, families of lines are identified on a detector according to a novel algorithm. Next, a computation of derivatives between neighboring projections occurs and is followed by a convolution of the derivatives with a filter along lines from the selected families of line. Next, using the filtered data, the image is updated by performing back projection. Finally, the preceding steps are repeated for each CB projection until an entire object has been scanned. This embodiment works with keeping several (approximately 2–4) CB projections in memory at a time and uses one family of lines.

For the second embodiment, different families of lines can be used in combination with keeping several CB projections in memory.

Modifications of these embodiments are possible, that will allow keeping only one CB projection in computer memory at a time. This can be done analogously to what was done in U.S. patent application Ser. No. 10/143,160 filed May 10, 2002, which is incorporated by reference, which claims the benefit of priority to U.S. Provisional Application 60/312,827 filed Aug. 16, 2001.

Consequently, the new algorithms allow to slow the patient down by about a factor of three, but still use the same size detector array.

Further objects and advantages of this invention will be apparent from the following detailed description of the presently preferred embodiments, which are illustrated schematically in the accompanying drawings.

BRIEF DESCRIPTION OF THE FIGURES

FIG. 18 is a three substep flow chart for finding families of lines for filtering, which corresponds to step 20 of FIG. 2.

DESCRIPTION OF THE PREFERRED EMBODIMENTS

Figure 1:
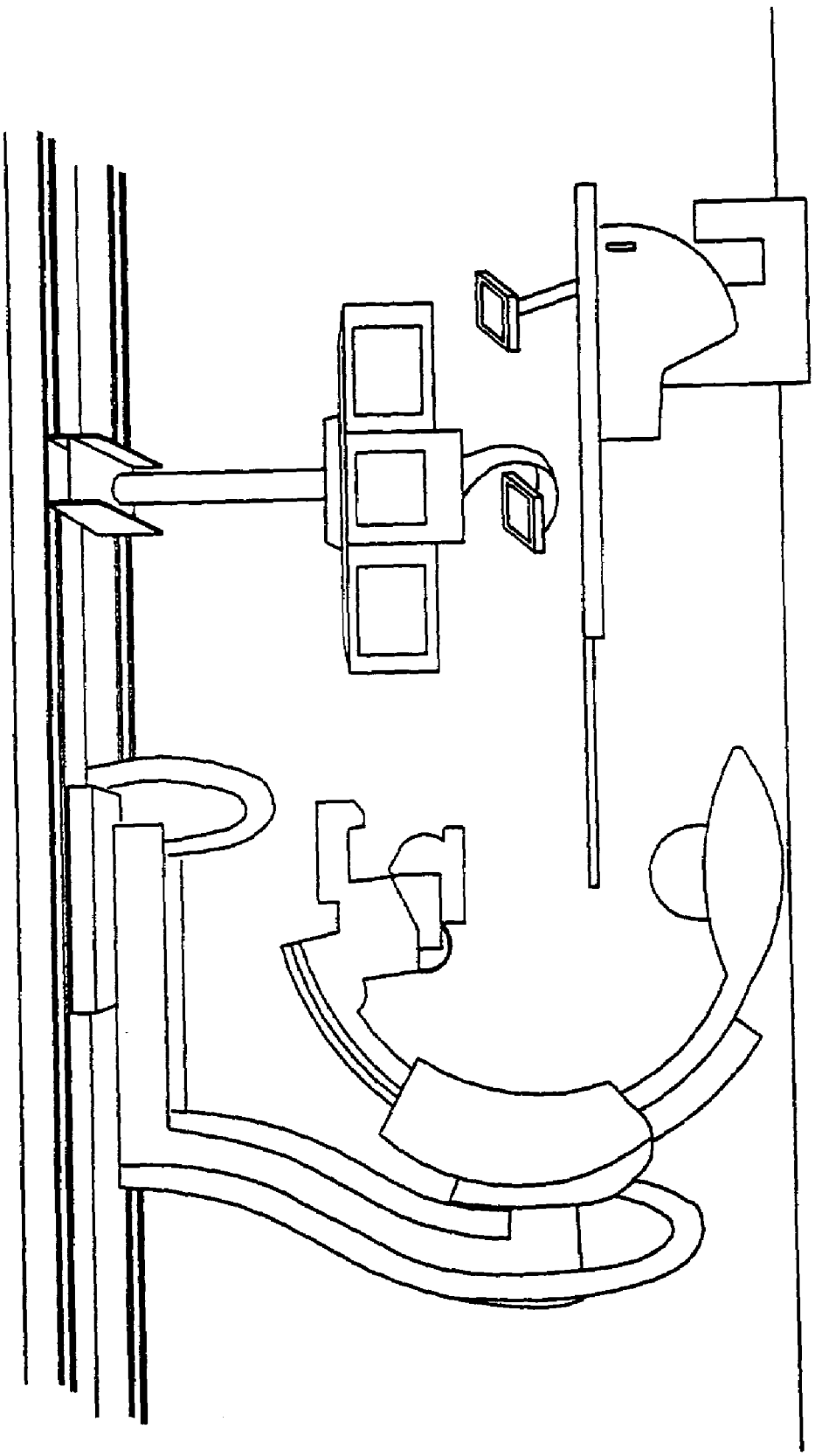
FIG. 1 shows a typical arrangement of a patient on a table that moves within a rotating gantry having an x-ray tube source and a detector array, where cone beam projection data sets are received by the x-ray detector, and an image reconstruction process takes place in a computer with a display for the reconstructed image.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

This invention is a continuation-in-part of U.S. patent application Ser. No. 10/143,160 filed May 10, 2002, now U.S. Pat. No. 6,574,299, which is incorporated by reference, which claims the benefit of priority to U.S. Provisional Application 60/312,827 filed Aug. 16, 2001.

The invention will now be described in more detail.

Theoretical Background

First we introduce the necessary notations. Let $$C := \{y \in R^3 : y_1 = R\cos(s),\ y_2 = R\sin(s),\ y_3 = s(h/2\pi),\ s \in R\}, \tag{1}$$

where h>0 be a spiral, and U be an open set strictly inside the spiral:

$$\overline{U} \subset \{x \in R^3 : x_1^2 + x_2^2 < r^2\},\ 0 < r < R, \tag{2}$$

$S^2$ is the unit sphere in $R^3$, and $$D_f(y, \beta) := \int_0^\infty f(y + \beta t)\,dt,\ \beta \in S^2, \tag{3}$$

$$\beta(s, x) := \frac{x - y(s)}{|x - y(s)|},\ x \in U,\ s \in R, \tag{4}$$

$$\prod(x, \xi) := \{y \in R^3 : (y - x) \cdot \xi = 0\},$$

$\Pi(x,\xi) := \{y \in R^3 : (y-x)\cdot\xi = 0\}$, (4)

that is $D_f(y,\beta)$ is the CB transform of f. Given $(x,\xi) \in U \times (R^3, 0)$, let $s_j = s_j(\xi, \xi\cdot x)$, j=1,2, ..., denote points of intersection of the plane $\Pi(x,\xi)$ with C. Also, $\dot{y}(s) := dy/ds$. For $\beta \in S^2$, $\beta^\perp$ denotes the great circle $\{\alpha \in S^2 : \alpha\cdot\beta = 0\}$. Fix any $x \in R^3$, where f needs to be computed. In order to compute f(x) we will use a section of the spiral of finite extent, which is to be determined later. For now it will be denoted C(x). The corresponding parametric interval is denoted I(x). The main assumption about C(x) is the following.

Property C1. (Completeness condition) Any plane through x intersects C(x) at least at one point.

An important ingredient in the construction of the inversion formula is weight function $n(s,x,\alpha)$, $\alpha \in \beta^\perp(s,x)$. The function n can be understood as follows. x and $\alpha$ determine the plane $\Pi(x,\alpha)$, and the weight n assigned to $y(s) \in \Pi(x, \alpha) \cap C$ depends on the location of x. In view of this interpretation we assume $n(s,x,\alpha) = n(s,x,-\alpha)$. The main assumptions about n are the following.

Property W1. Normalization condition:

$$\sum_j n(s_j, x, \alpha) = 1\ a\cdot e\cdot on\ S^2; \tag{5}$$

Property W2. There exist finitely many $C^1$ functions $\alpha_k(s,x) \in \beta^\perp(s,x)$, $s \in I(x)$, such that $n(s,x,\alpha)$ is locally constant in a neighborhood of any $(s,\alpha)$, where $s \in I(x)$ and $\alpha \in \beta^\perp(s,x)$, $\alpha \notin \cup_k \alpha_k(s,x)$.

Denote $$\phi(s,x,\theta) := \text{sgn}(\alpha\cdot\dot{y}(s))n(s,x,\alpha),\ \alpha = \alpha(s,\theta) \in \beta^\perp(s,x), \tag{6}$$

Under assumptions C1, W1, and W2 the following general inversion formula is derived in the paper by A. Katsevich "A general scheme for constructing inversion algorithms for cone beam CT," International Journal of Mathematics and Mathematical Sciences, Vol. 21, pp. 1305–1321 (2003):

$$f(x) = -\frac{1}{4\pi^2} \int_{I(x)} \sum_m \frac{c_m(s,x)}{|x-y(s)|} \times \qquad (7)$$

$$\int_0^{2\pi} \frac{\partial}{\partial q} D_f(y(q), \cos\gamma\beta(s,x) + \sin\gamma\alpha^\perp(s,x,\theta_m))\bigg|_{q=s} \frac{d\gamma}{\sin\gamma} ds,$$

where $\theta_m \in [0, \pi)$ are the points where $\phi(s,x,\theta)$ is discontinuous, and $c_m(s,x)$ are values of the jumps:

$$c_m(s,x) := \lim_{\varepsilon \to 0^+} (\phi(s,x,\theta_m+\varepsilon) - \phi(s,x,\theta_m-\varepsilon)). \qquad (8)$$

Unless n is chosen appropriately, the inversion formula is not necessarily of the FBP type.

3PI Lines and Their Properties

Figure 3:
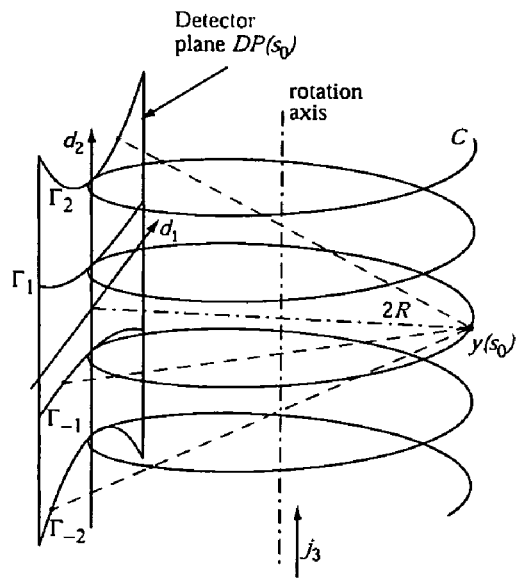
FIG. 3 shows stereographic projection of the spiral onto the detector plane
Figure 4:
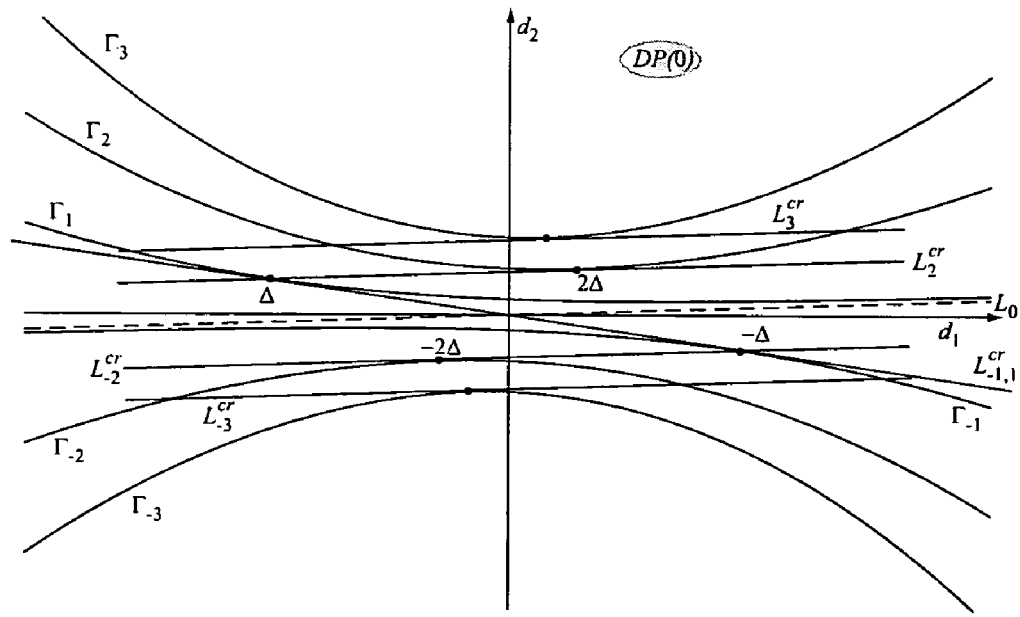
FIG. 4 shows the detector plane with various projections and important lines

Suppose that the x-ray source is fixed at $y(s_0)$ for some $s_0 \in \mathbb{R}$. Since the detector array rotates together with the source, the detector plane depends on $s_0$ and is denoted $DP(s_0)$. It is assumed that $DP(s_0)$ is parallel to the axis of the spiral and is tangent to the cylinder $y_1^2 + y_2^2 = R^2$ (cf. (1)) at the point opposite to the source. Thus, the distance between $y(s_0)$ and the detector plane is 2R (see FIG. 3). Introduce coordinates in the detector plane as follows. Let the $d_1$-axis be perpendicular to the axis of the spiral, the $d_2$-axis be parallel to it, and the origin coincide with the projection of $y(s_0)$. Project stereographically the upper and lower turns of the spiral onto the detector plane as shown in FIG. 3. This gives the following parametric curves:

$$d_1(s) = 2R\frac{\sin(s-s_0)}{1-\cos(s-s_0)}, \quad d_2(s) = \frac{h}{\pi}\frac{s-s_0}{1-\cos(s-s_0)}, \qquad (9)$$

$$\rho + 2\pi(j-1) \leq s-s_0 \leq 2\pi j - \rho, j \geq 1, \text{ or} \qquad (10)$$

$$\rho + 2\pi j \leq s-s_0 \leq 2\pi(j+1) - \rho, j \leq -1, \qquad (11)$$

where $\rho$ is determined by the radius of support of the patient: $\rho = 2\cos^{-1}(r/R)$ (cf. (2)). These curves are denoted $\Gamma_j$, $j = \pm 1, \pm 2, \ldots$ (see FIG. 4). $\hat{x}$ denotes the projection of x. Connect an arbitrary source position $y(s_0)$ to all points $y(s)$ on the spiral, where $$2\pi < s-s_0 < 4\pi \text{ or } -4\pi < s-s_0 < -2\pi. \qquad (12)$$

Figure 5:
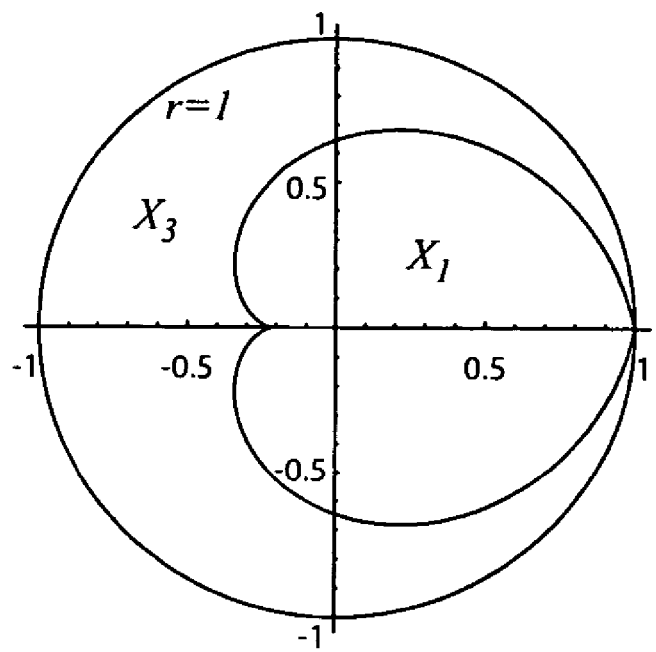
FIG. 5 shows the boundary curve

This gives two surfaces, which are denoted $S_U^{3PI}(s_0)$ and $S_L^{3PI}(s_0)$. The region bounded by the two surfaces and the cylinder $x_1^2 + x_2^2 = R^2$ is denoted $V_{3PI}(s_0)$. Let x be fixed. If $s_0$ is sufficiently small, then $S_U^{3PI}(s_0)$ is below x. As $s_0$ increases, two cases are possible. In the first one, known as continuous illumination, x enters $V^{3PI}(s_0)$ through $S_U^{3PI}(s_0)$ and leaves $V^{3PI}(s_0)$ through $S_L^{3PI}(s_0)$. Clearly, the above procedure yields a unique 3PI interval $[b_0(x), t_0(x)]$ and the corresponding unique 3PI line $L_0^{3PI}(x)$. In the second case, known as interrupted illumination, x enters and leaves $V^{3PI}(s_0)$ several times. More precisely, x intersects each of the surfaces $S_U^{3PI}(s_0)$ and $S_L^{3PI}(s_0)$ exactly three times. Therefore, the above procedure now gives three 3PI lines $L_i^{3PI}(x), i=1,2,3$. The corresponding values of the parameter are denoted $b_i(x)$, $t_i(x)$, $i=1,2,3$. Due to the symmetry of the spiral, if x leaves (enters) $V^{3PI}(s_0)$ when $s_0 = b_i(x)$, then x enters (leaves) $V^{3PI}(s_0)$ when $s_0 = t_i(x)$, $i=1,2,3$. Consider the plane $x_3 = 0$. The boundary between the two cases is shown in FIG. 5. We see that the curve has no self intersections, so it divides the open disk $x_1^2 + x_2^2 < 1$ into two regions: $X_1$ and $X_3$. In the central one, denoted $X_1$, there is one 3PI line for each x. In the exterior one, denoted $X_3$, there are three 3PI line for each x.

The following properties can be established. If there is only one 3PI line for a point x, then $$x \in V^{3PI}(s_0) \Leftrightarrow s_0 \in I^{3PI}(x) := [b_0, t_0], \qquad (13a)$$

$$2\pi < t_i - b_i < 4\pi, \; i=1,2,3. \qquad (14a)$$

If there are three 3PI lines for a point x, then $$x \in V^{3PI}(s_0) \Leftrightarrow s_0 \in I^{3PI}(x) := [b_1, b_2] \cup [b_3, t_1] \cup [t_2, t_3], \qquad (13b)$$

$$2\pi < t_i - b_i < 4\pi, \; i=1,2,3. \qquad (14b)$$

In terms of the detector plane equations (13a) and (13b) imply that $\hat{x}$ is between $\Gamma_2$ and $\Gamma_{-2}$ if and only if $s \in I^{3PI}(x)$. Therefore, using the analogy with the 1PI case, we can call this region on the detector the 3PI window. In the 1PI case, the parametric interval bounded by the endpoints of the 1PI line of x is called the 1PI parametric interval of x. Similarly, $I^{3PI}(x)$ is called the 3PI parametric interval of x.

An Auxiliary Construction

Suppose first that continuous illumination takes place. Consider the following two curves on the surface of the unit sphere $S^2$. This first curve consists of all unit vectors $\alpha$ orthogonal to $L_0^{3PI}(x)$ and is denoted by A. The other curve consists of vectors $$\alpha(s) = \pm \frac{(x-y(s)) \times \dot{y}(s)}{|(x-y(s)) \times \dot{y}(s)|}, \quad s \in I^{3PI}(x), \qquad (15)$$

and is denoted by T. It is not convenient to represent these curves directly on $S^2$, so they will be shown on the plane using spherical coordinates $(\theta_1, \theta_2)$ defined by $$S^2 \ni \alpha(s) = (\cos\theta_1 \sin\theta_2, \sin\theta_1 \sin\theta_2, \cos\theta_2),$$
$$-\pi \leq \theta_1 \leq \pi, 0 \leq \theta_2 < \pi. \qquad (16)$$

Since both $\alpha$ and $-\alpha$ define the same plane, we can restrict $\theta_1$ to any interval of length $\pi$ and "glue" the opposite boundaries using the identification $$(\theta_1, \theta_2) \equiv (\theta_1 + \pi)_{mod 2\pi}, \pi - \theta_2). \qquad (17)$$

Figure 6:
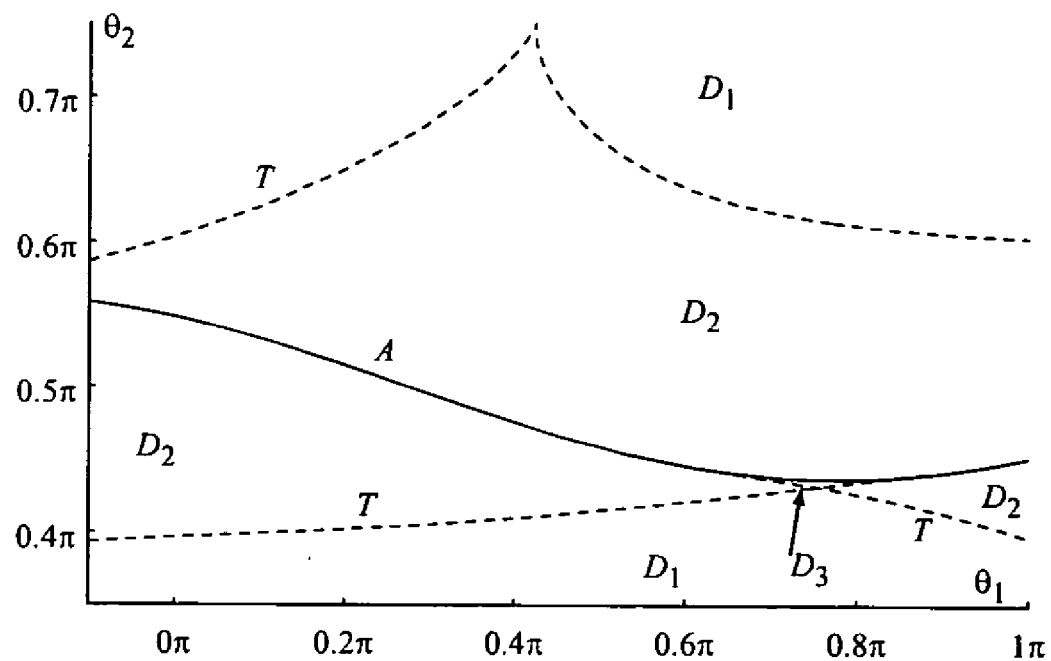
FIG. 6 shows the continuous illumination case, x/R=(0, 0.25, 0)

A typical situation for $x/R = (0, 0.25, 0)$ is shown in FIG. 6. It is very convenient to think about points on $S^2$ not only as unit vectors, but also as planes. Each $\alpha \in S^2$ corresponds to a unique plane through x with normal vector $\alpha$. This correspondence is one-to-one if vectors with opposite orientation are identified. Together A and T split $S^2$ into several domains: $D_1, D_2, \ldots$ By construction, for a fixed i, the number of points in $C^{3PI}(x) \cap \Pi(x,\alpha)$ is the same for all $\alpha \in D_i$. If $D_i$ contains k intersection points (IPs), it will be called a k IP domain.

Suppose now that interrupted illumination takes place. In a similar fashion, define several curves on the surface of $S_2$. The first three curves are obtained by considering unit vectors perpendicular to each of the three 3PI axes. They are denoted $A_k$, $k=1,2,3$. The second set of curves is obtained by restricting s in (15) to the intervals $[b_1, b_2]$, $[b_3, t_1]$, and

Figure 7:
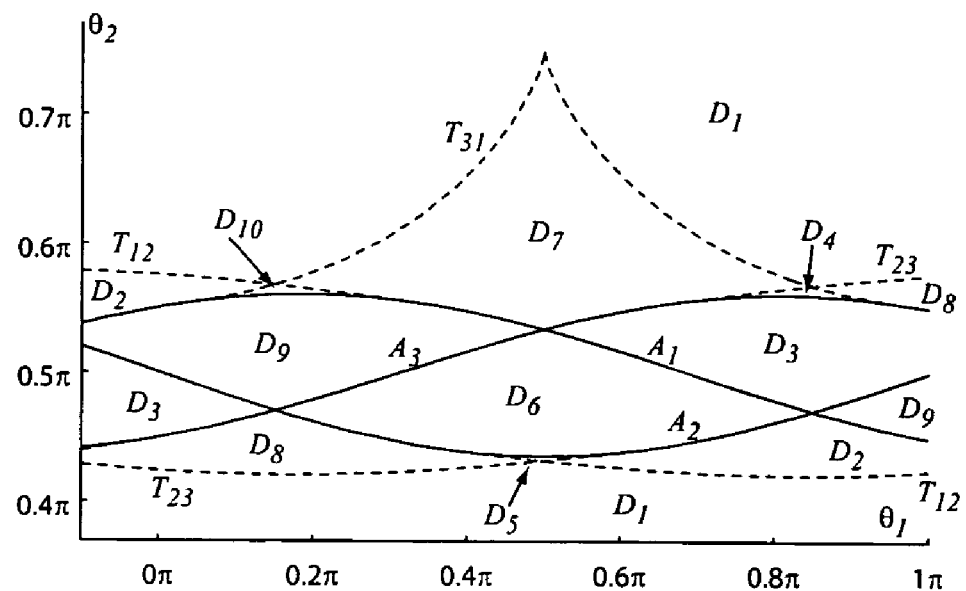
FIG. 7 shows the interrupted illumination case, x/R= (−0.5, 0, 0)

[t$_2$,t$_3$]. These curves are denoted T$_{12}$, T$_{31}$, and T$_{23}$, respectively. A typical situation for x/R=(−0.5,0,0) is shown in FIG. 7.

Figure 8:
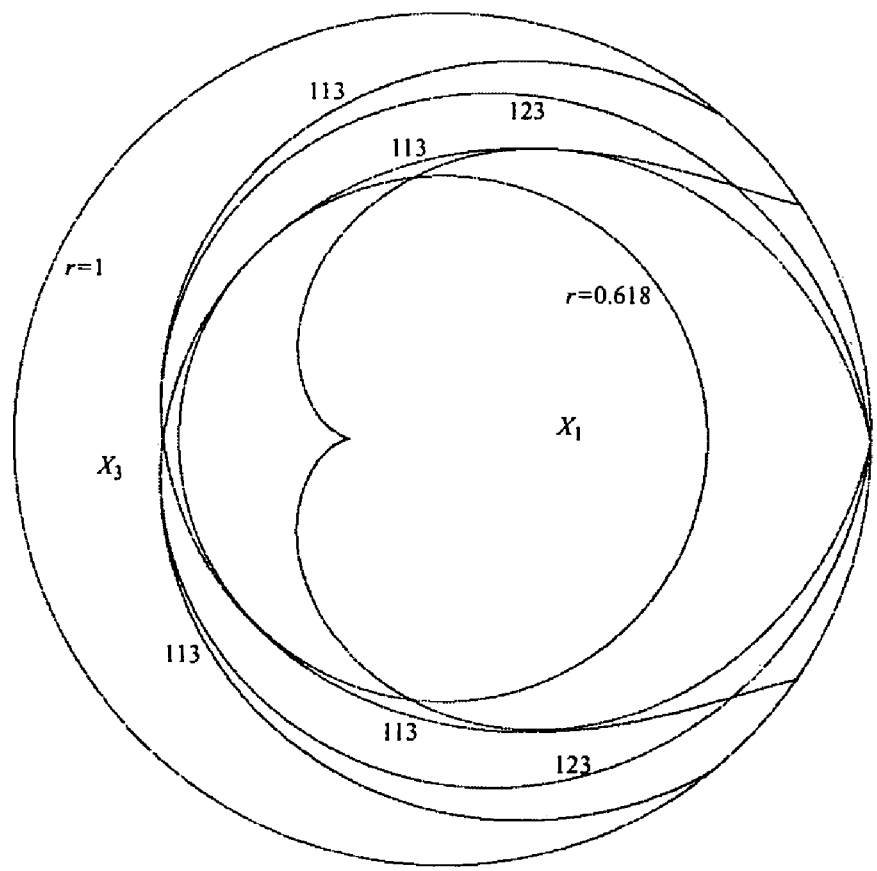
FIG. 8 shows the points where various critical events occur

It is clear that if x$_1$ and x$_2$ are close to each other, they will share similar diagrams. By this we mean that by a smooth sequence of transformations one diagram can be converted into the other, and in corresponding domains the number of IPs and their distribution over the subintervals in I$^{3PI}$ stays the same. An essential change is possible only in a neighborhood of x where a "critical event" occurs: three boundaries intersect each other at one point on S$^2$. These points can be found numerically and the results are shown in FIG. 8. The smallest distance from any of these points to the center of rotation is r0≈0.618R. Thus, in situations of interest in medical applications (r$_{FOV}$≦0.5R), only the following two cases can happen: continuous illumination as shown in FIG. 6 and interrupted illumination as shown in FIG. 7.

Construction of the Weight Function n

Figure 9:
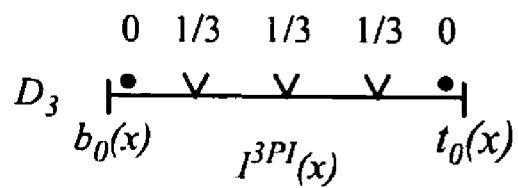
FIG. 9 shows the distribution of weights inside the 5IP domain in the case of continuous illumination
Figure 10:
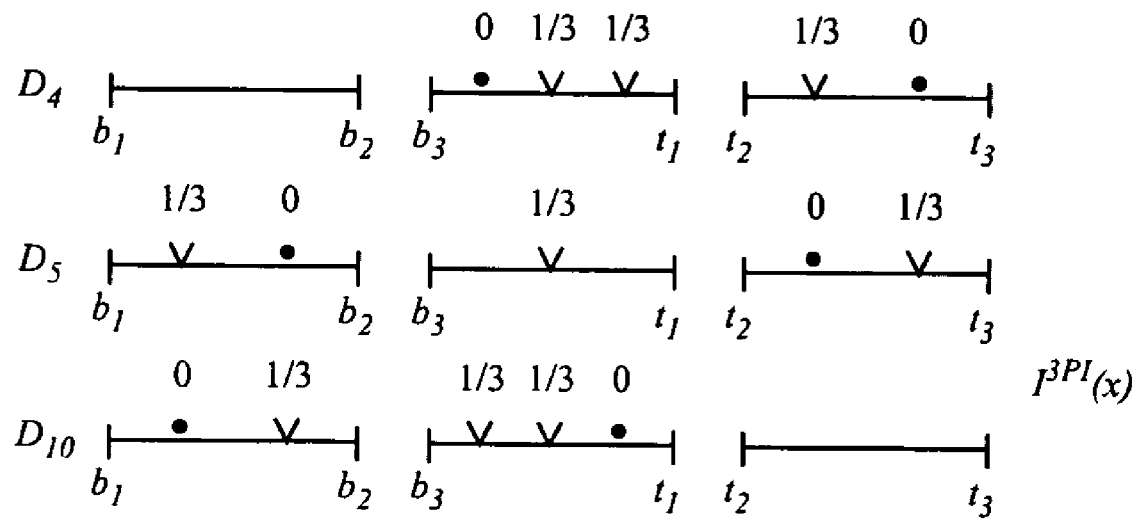
FIG. 10 shows the distribution of weights inside the 5IP domains in the case of interrupted illumination

For any s∈I$^{3PI}$(x) determine the weight function n(s,x,α), α∈β$^{\perp}$(s,x), according to the following rule:

In 1IP domains the only IP gets weight n=1;

In 3IP domains each IP gets weight n=⅓;

In 5IP domains two IPs get weight n=0, and all the remaining IPs get weight n=⅓ (see FIGS. 9 and 10).

First Reconstruction Algorithm

Once the weights are found, we have all the ingredients needed for constructing the algorithm. First of all, for image reconstruction at x we take the 3PI spiral segment of x: C(x)=C$^{3PI}$(x) and I(x)=I$^{3PI}$(x) (cf. Section 1). As follows from (6), (7), for each s∈I$^{3PI}$(x) the filtering directions are determined by finding the discontinuities of ϕ(s,x,α)=sgn(α·ẏ(s))n(s,x,α). The study of these discontinuities leads us to the following three families of lines.

Figure 11:
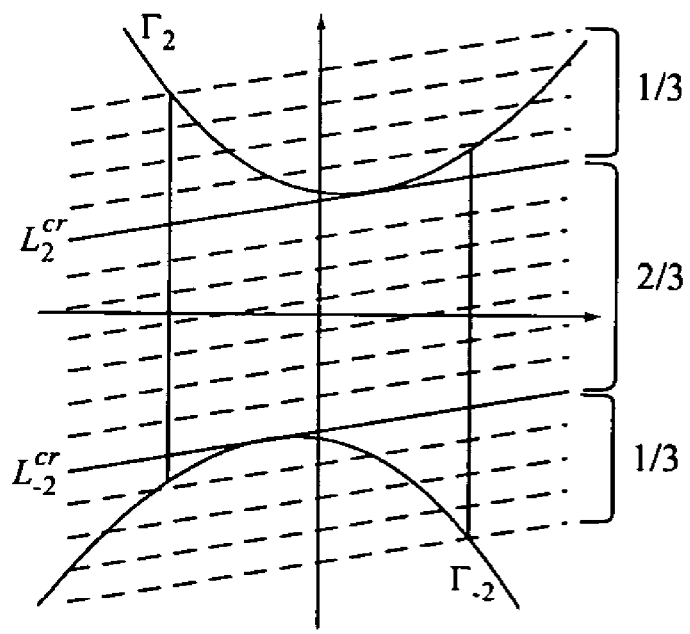
FIG. 11 shows the family of filtering lines parallel to $L_0$

The first family consists of lines parallel to the spiral tangent. This family is denoted $\mathcal{L}_0$. The lines and the associated coefficients c$_m$ are shown in FIG. 11. Obviously, for any x̂ there is only one line L∈$\mathcal{L}_0$ that contains x̂.

Figure 12:
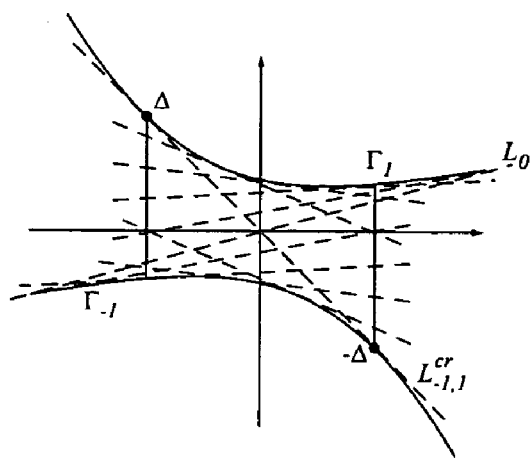
FIG. 12 shows the family of filtering lines tangent to $\Gamma_{\pm 1}$
Figure 13:
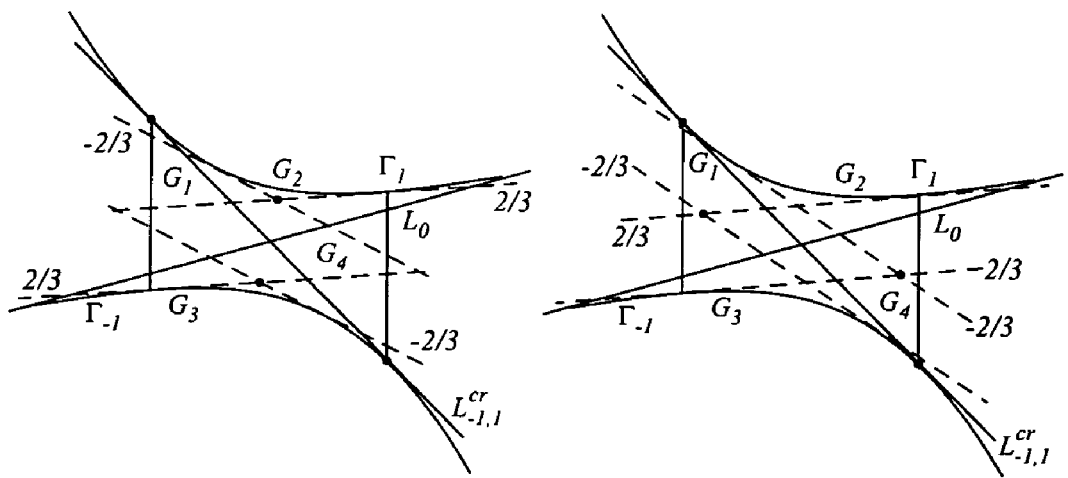
FIG. 13 shows how to choose filtering lines depending on the location of $\hat{x}$

In FIG. 12 we see the second family of filtering lines. It consists of lines tangent to Γ$_{±1}$ and is denoted $\mathcal{L}_{±1}$. Here for each x̂ within the 1PI window we take two lines from $\mathcal{L}_{±1}$. These lines are determined from the rule explained in FIG. 13. This figure also shows the associated coefficients c$_m$.

Figure 14:
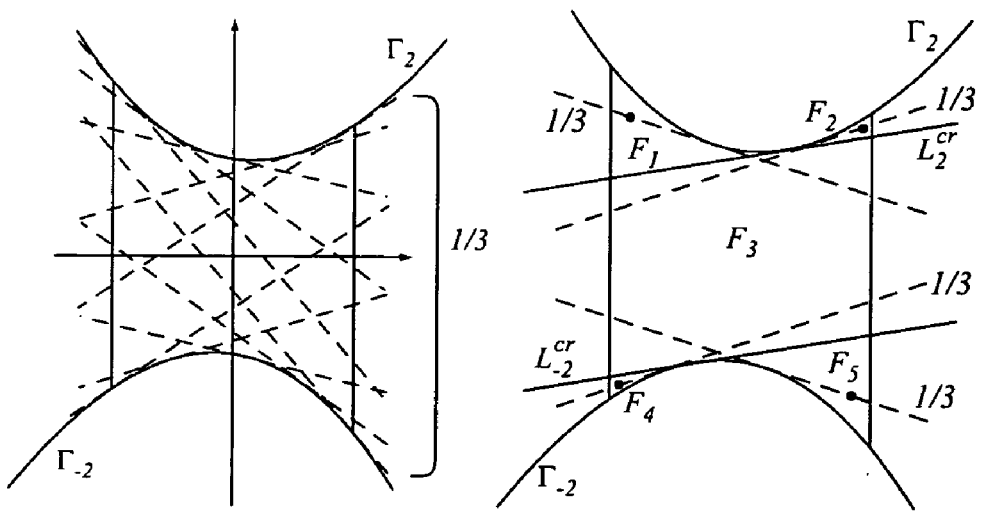
FIG. 14 shows the family of filtering lines tangent to $\Gamma_{\pm 2}$

In FIG. 14 (left panel) we see the family of filtering lines tangent to Γ$_{±2}$. This family is be denoted $\mathcal{L}_{±2}$. Now, for any x̂∈F$_1$∪F$_2$∪F$_4$∪F$_5$ there might be more than one line L∈L$_2$ that contains x̂. The unique line is determined from the following rule (see FIG. 14, right panel). If x̂∈F$_1$∪F$_4$, the point of tangency is to the right of x̂. If x̂∈F$_2$∪F$_5$, the point of tangency is to the left of x̂. In all cases c$_m$=⅓.

Figure 15:
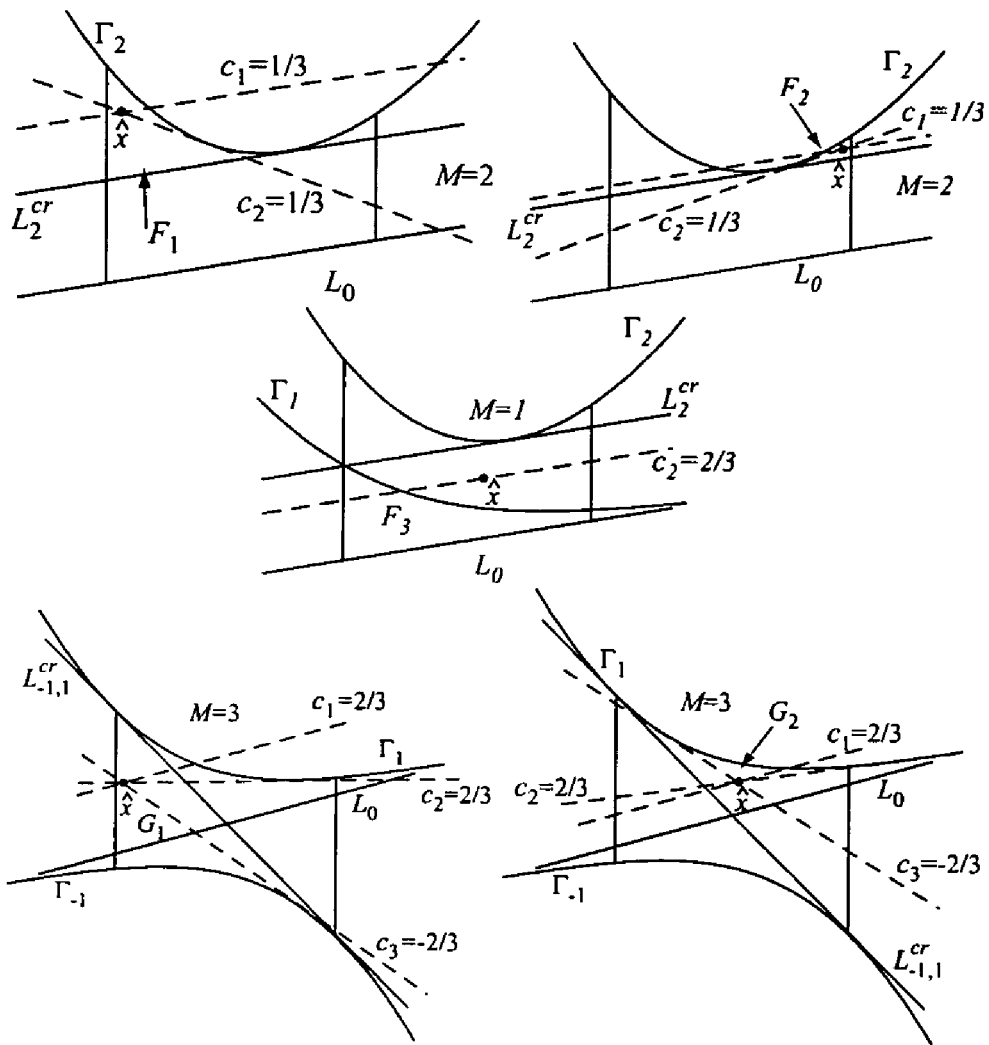
FIG. 15 shows the filtering lines and the associated constants $c_m$ in different cases: $\hat{x} \in F_1$ (top left panel), $\hat{x} \in F_2$ (top right panel), $\hat{x} \in F_3$ and above $\Gamma_1$ (middle panel), $\hat{x} \in G_1$ (bottom left panel), $\hat{x} \in G_2$ (bottom right panel).

FIG. 15 summarizes the information contained in FIGS. 11–14. It shows all possible cases where x̂ might be and all the associated filtering directions and constants c$_m$. In all cases the direction of filtering as assumed to be from left to right. It follows from our construction (cf. FIG. 15) that θ$_m$(s,x) and c$_m$(s,x) in the general reconstruction formula (7), (8) depend on x only via β(s,x). Therefore, we can replace x by β(s,x) in the arguments of c$_m$ and α$^{\perp}$ and rewrite (7) in the form $$f(x) = -\frac{1}{4\pi^2} \int_{I^{3PI}(x)} \frac{1}{|x-y(s)|} \sum_{m=1}^{M(s,\beta)} c_m(s,\beta) \Psi_m(s,\beta(s,x)) ds, \quad (18)$$

$$\Psi_m(s,\beta) := \int_0^{2\pi} \frac{\partial}{\partial q} D_f(y(q), \cos\gamma\beta + \sin\gamma\alpha^{\perp}(s,\beta,\theta_m))\Big|_{q=s} \frac{d\gamma}{\sin\gamma} ds, \quad (19)$$

$x_1^2+x_2^2 \leq (0.618R)^2. \quad (20)$

Step 31. Fix a line L from the said set of lines obtained in Step 20. Note also that given a filtering line L, all x whose projections belong to L and satisfy the rules mentioned above share the same filtering line L (cf. FIG. 15). Thus, (19) becomes a convolution, (18) becomes backprojection, and the algorithm (18), (19) is of the convolution-based FBP type. This can be seen similarly to U.S. patent application Ser. No. 10/143,160 filed May 10, 2002, which is incorporated by reference. Other methods and techniques for backprojection can be used. See additionally, for example, U.S. Pat. No. 6,574,299 to Katsevich, which is incorporated by reference.

Improved Reconstruction Algorithm

Let ψ(t) be any smooth function defined on R and with the properties ψ(0)=0, ψ'(t)>0, t∈R. Define the new family of lines $\mathcal{L}'_2$ by requesting that any given line L∈$\mathcal{L}'_2$ has three points of intersection with Γ$_{±1}$∪Γ$_{±2}$: s$_1$,s$_2$,s$_3$, and these points satisfy:

$s_1-s=\psi(s_3-s_2), s+2\pi<s_3<s+4\pi,$ (21)

$s_3-s_2=\psi(s_1-s), s-4\pi<s_3<s-2\pi.$ (22)

Figure 16:
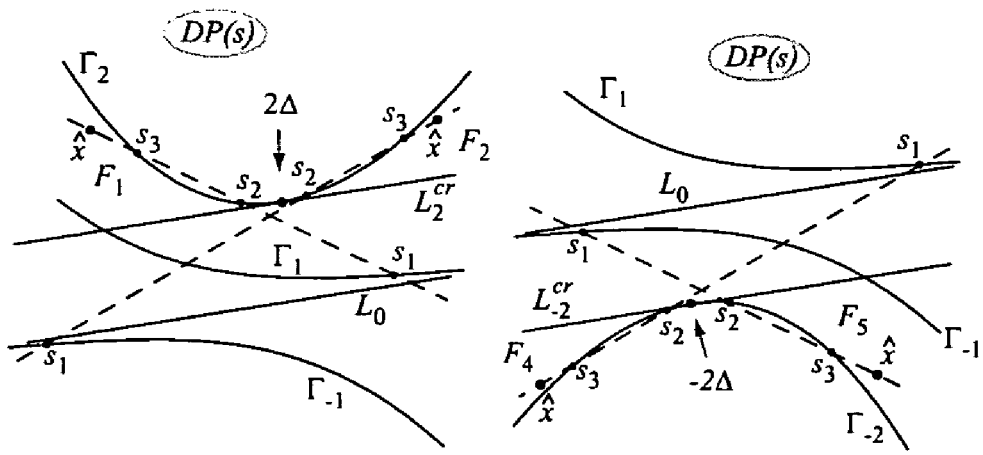
FIG. 16 shows possible locations of points $s_1, s_2, s_3$

Recall that s is the current source position. The lines L∈$\mathcal{L}'_2$ can be parameterized, for example, by s$_3$, 2π<|s$_3$|<4π. Location of s$_1$ and s$_2$ depends on where s$_3$ is and is illustrated in FIG. 16.

Using the properties of ψ it is easy to establish that for each x̂∈F$_1$∪F$_2$∪F$_4$∪F$_5$ there is a unique L∈$\mathcal{L}'_2$ that contains x̂. Also, if x̂→L$_2$$^{cr}$, then s$_2$,s$_3$→2Δ and s$_1$→s. Similarly, if x̂→L$_{-2}$$^{cr}$, then s$_2$,s$_3$→−2Δ and s$_1$→s.

More importantly, in the case x̂∈F$_1$∪F$_2$∪F$_4$∪F$_5$ it is possible to reduce the number of filtering directions from two to one. The additional benefit is the improved detector usage. Thus, the top two panels shown in FIG. 15 should be replaced by the diagrams shown in FIG. 17. The case when x̂ appears below L$_0$(i.e., x̂∈F$_4$∪F$_5$) can be obtained from FIG. 17 by symmetry with respect to the origin in the detector plane.

The form of the inversion formula (18), (19), remains the same. The first difference is that M(s,β)=1 (instead of 2) when x̂∈F$_1$∪F$_2$∪F$_4$∪F$_5$. The second difference is the direction of filtering, which is now determined from (21), (22).

General Overview of the Reconstruction Algorithms

Figure 2:
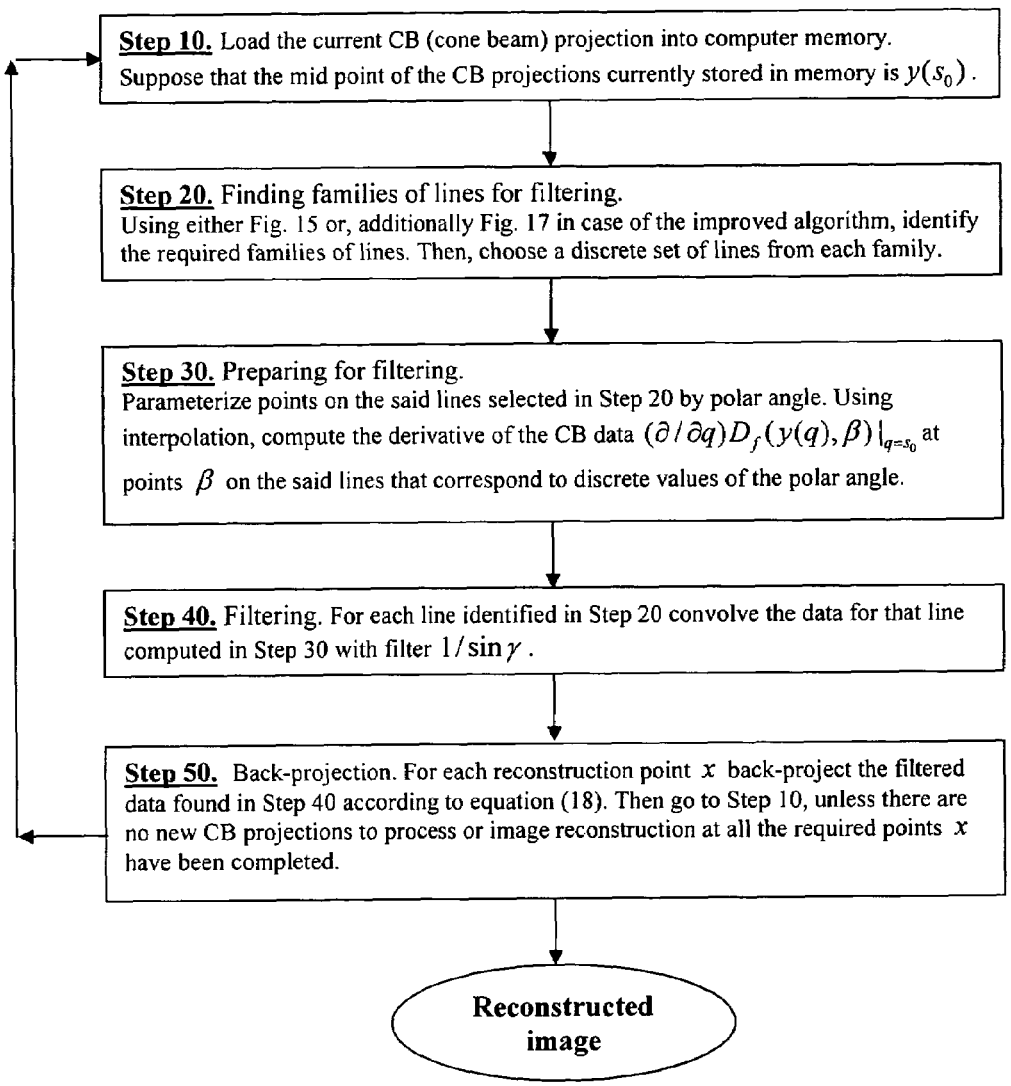
FIG. 2 shows an overview of the basic process steps of the invention.

FIG. 2 shows an overview of the basic process steps 10, 20, 30, 40, 50 of the invention. The steps will now be described.

Step 10. Load the current CB (cone beam) projection into computer memory. Suppose that the mid point of the CB projections currently stored in memory is y(s$_0$).

Step 20. Finding families of lines for filtering.

Figure 17:
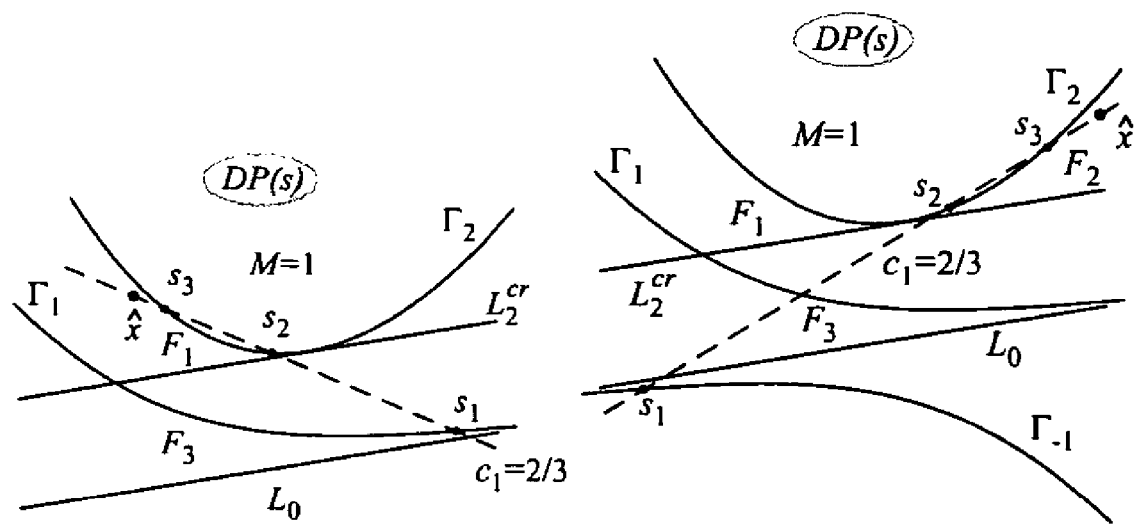
FIG. 17 shows the filtering lines and the associated constants $c_m$ in different cases: $\hat{x} \in F_1$ (left panel), $\hat{x} \in F_2$ (right panel).
Figure 19:
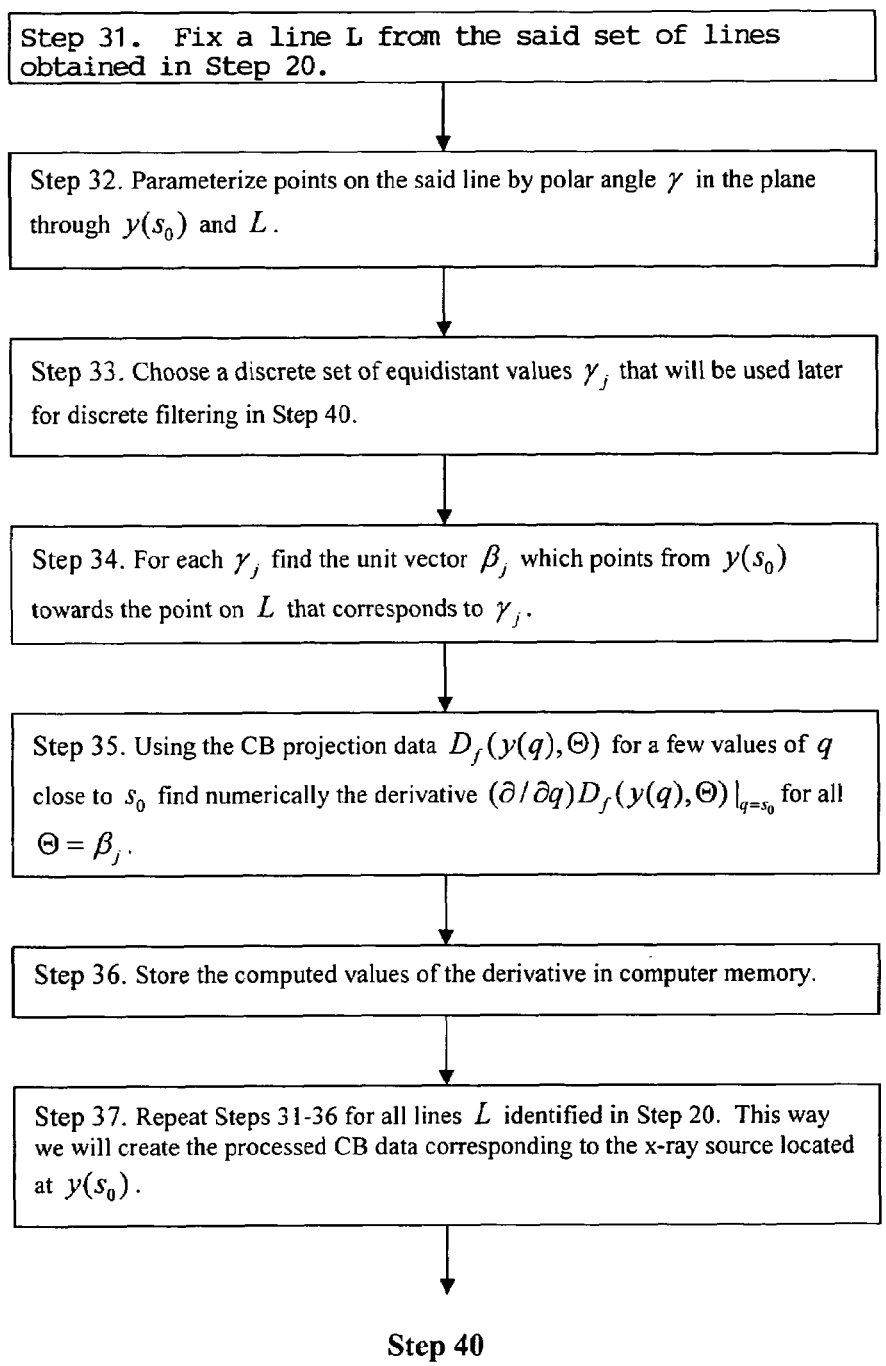
FIG. 19 is a seven substep flow chart for preparing for filtering, which corresponds to step 30 of FIG. 2.
Figure 20:
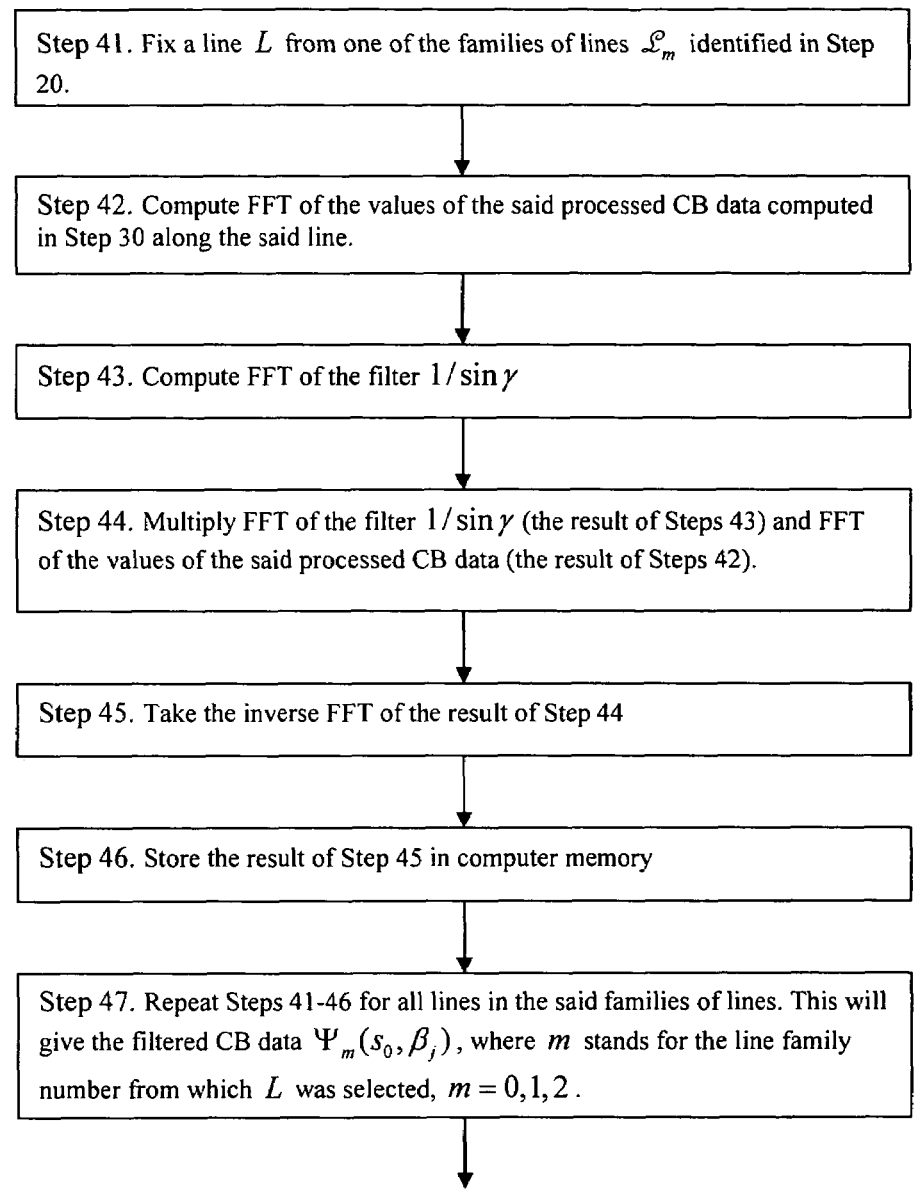
FIG. 20 is a seven substep flow chart for filtering, which corresponds to step 40 of FIG. 2.
Figure 21:
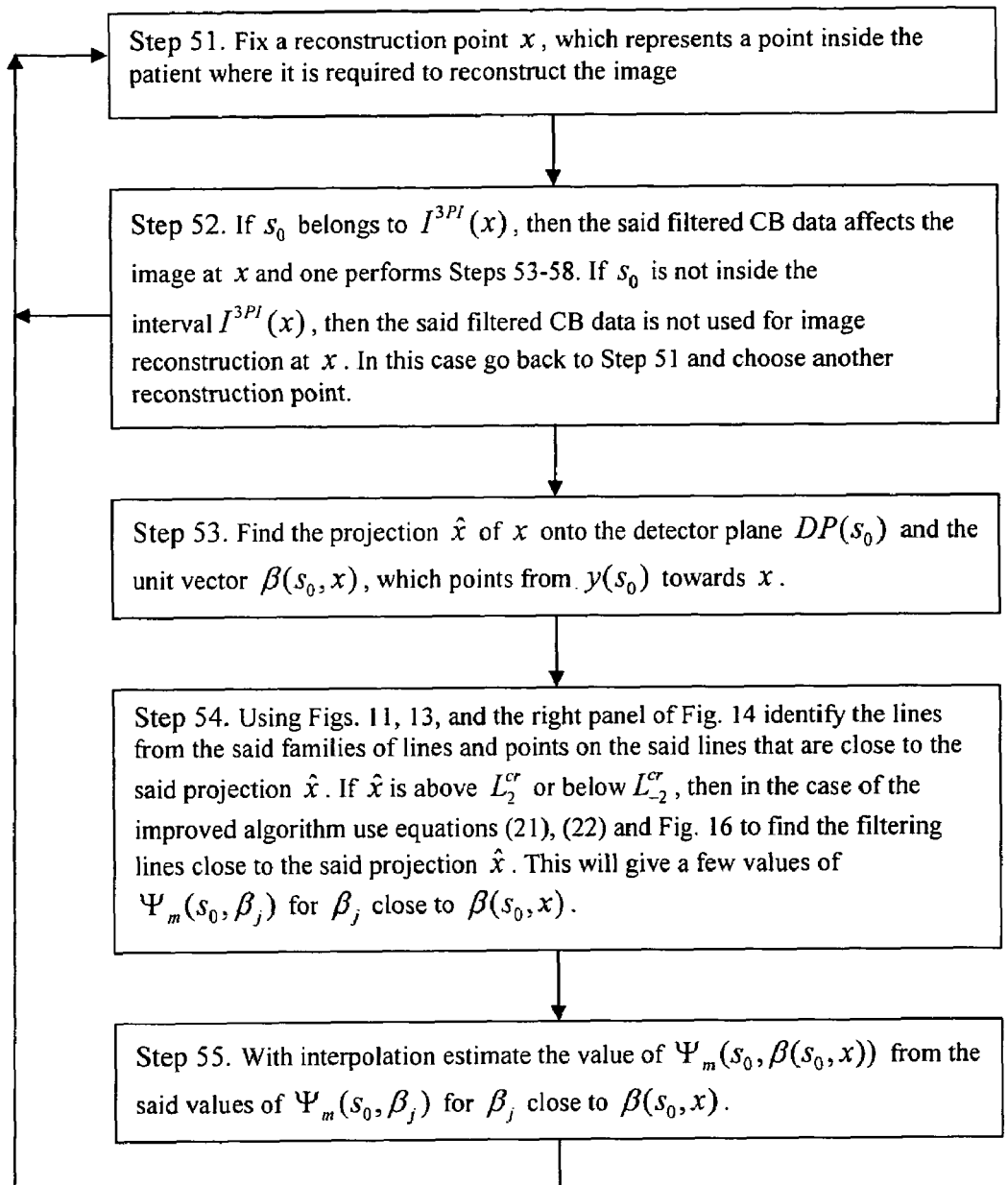
FIG. 21 is a five substep flow chart for the first part of back-projection, which corresponds to step 50 of FIG. 2.
Figure 22:
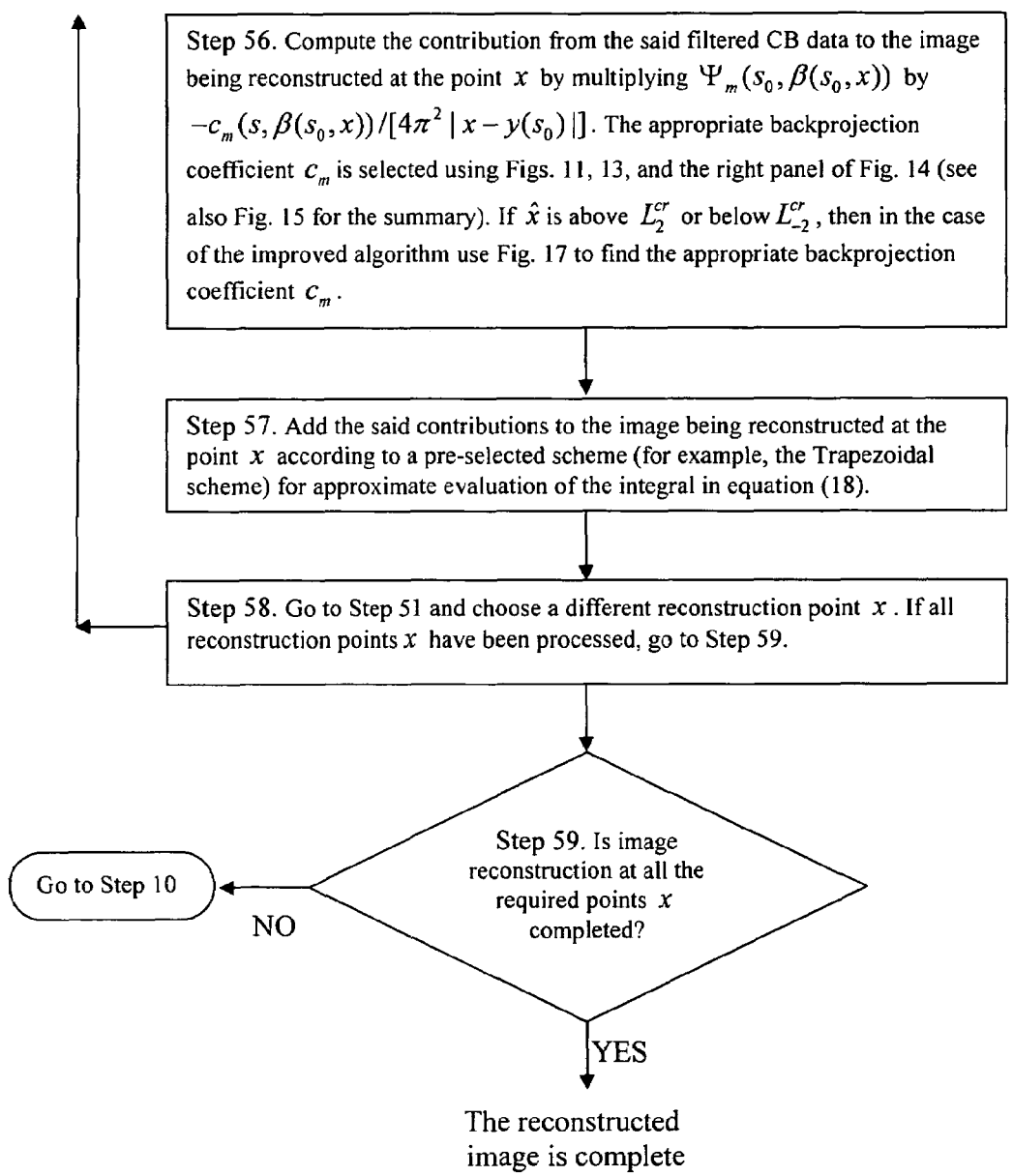
FIG. 22 is a three substep flow chart for the second part of back-projection, which corresponds to step 50 of FIG. 2.

Using either FIG. 15 or, additionally FIG. 17 in case of the improved algorithm, identify the required families of lines. Then, choose a discrete set of lines from each family.

Step 30. Preparing for filtering.
  Parameterize points on the said lines selected in Step 20 by polar angle. Using interpolation compute the derivative of the CB data $(\partial/\partial q)D_f(y(q),\beta)|_{q=s_0}$ at points $\beta$ on the said lines that correspond to discrete values of the polar angle.
Step 40. Filtering. For each line identified in Step 20 convolve the data for that line computed in Step 30 with filter 1/sin $\gamma$.
Step 50. Back-projection. For each reconstruction point x back-project the filtered data found in Step 40 according to equation (18). Then go to Step 10, unless there are no new CB projections to process or image reconstruction at all the required points x have been completed.

Now we describe the algorithm in detail following the five steps 10–50 shown in FIG. 2.
Step 10. Load the current CB (cone beam) projection into computer memory. Suppose that the mid point of the CB projections currently stored in memory is $y(s_0)$. The detector plane corresponding to the x-ray source located at $y(s_0)$ is denoted $DP(s_0)$.
Step 20. Finding families of lines for filtering.
  The set of lines can be selected by the following substeps 21, 22, and 23.
    Step 21. From the family of lines $\mathscr{L}_0$ choose an equidistant set of lines that are parallel to the spiral tangent and that cover the projection of the region of interest onto the detector plane located between $\Gamma_2$ and $\Gamma_{-2}$ (see FIG. 11).
    Step 22. From the family of lines $\mathscr{L}_1$ choose a discrete set of lines that are tangent to $\Gamma_1$ and $\Gamma_{-1}$ (see FIG. 12). The extreme left point of tangency on $\Gamma_1$ does not have to extend beyond the projection of the region of interest onto the detector plane. Similarly, the extreme right point of tangency on $\Gamma_{-1}$ does not have to extend beyond the projection of the region of interest onto the detector plane.
    Step 23. From the family of lines $\mathscr{L}_2$ choose a discrete set of lines that are tangent to $\Gamma_2$ and $\Gamma_{-2}$ (see FIG. 14, left panel). In both cases the points of tangency do not have to extend beyond the projection of the region of interest onto the detector plane.
  In case of the improved algorithm, instead of the lines tangent to $\Gamma_2$ and $\Gamma_{-2}$, we choose a discrete (say, equidistant) set of values for $s_3$ on the curves $\Gamma_2$ and $\Gamma_{-2}$ and then determine the lines $L \in \mathscr{L}'_2$ by solving equations (21), (22). On both curves the points $s_3$ do not have to extend beyond the projection of the region of interest onto the detector plane.
Step 30. Preparing for filtering
  Step 31. Fix a line L from the said set of lines obtained in Step 20.
  Step 32. Parameterize points on the said line by polar angle $\gamma$ in the plane through $y(s_0)$ and L.
  Step 33. Choose a discrete set of equidistant values $\gamma_j$ that will be used later for discrete filtering in Step 40.
  Step 34. For each $\gamma_j$ find the unit vector $\beta_j$ which points from $y(s_0)$ towards the point on L that corresponds to $\gamma_j$.
  Step 35. Using the CB projection data $D_f(y(q), \Theta))$ for a few values of q close to $s_0$ find numerically the derivative $(\partial/\partial q)D_f(y(q), \Theta)|_{q=s_0}$ for all $\Theta=\beta_j$.
  Step 36. Store the computed values of the derivative in computer memory.
  Step 37. Repeat Steps 31–36 for all lines L identified in Step 20. This way we will create the processed CB data corresponding to the x-ray source located at $Y(s_0)$.

Step 40. Filtering
  Step 41. Fix a line L from one of the families of lines $\mathscr{L}_m$ identified in Step 20.
  Step 42. Compute FFT of the values of the said processed CB data computed in Step 30 along the said line.
  Step 43. Compute FFT of the filter 1/sin $\gamma$
  Step 44. Multiply FFT of the filter 1/sin $\gamma$ (the result of Steps 43) and FFT of the values of the said processed CB data (the result of Steps 42).
  Step 45. Take the inverse FFT of the result of Step 44.
  Step 46. Store the result of Step 45 in computer memory.
  Step 47. Repeat Steps 41–46 for all lines in the said families of lines. This will give the filtered CB data $\Psi_m(s_0,\beta_j)$, where m stands for the line family number from which L was selected, m=0,1,2.
  By itself the filtering step is well known in the field and can be implemented, for example, as shown and described in U.S. Pat. No. 5,881,123 to Tam, which is incorporated by reference.
Step 50. Back-projection
  Step 51. Fix a reconstruction point x, which represents a point inside the patient where it is required to reconstruct the image.
  Step 52. If $s_0$ belongs to $I^{3PI}(x)$, then the said filtered CB data affects the image at x and one performs Steps 53–58. If so is not inside the interval $I^{3PI}(x)$, then the said filtered CB data is not used for image reconstruction at x. In this case go back to Step 51 and choose another reconstruction point.
  Step 53. Find the projection $\hat{x}$ of x onto the detector plane $DP(s_0)$ and the unit vector $\beta(s_0,x)$, which points from $y(s_0)$ towards x.
  Step 54. Using FIGS. 11, 13, and the right panel of FIG. 14 identify the lines from the said families of lines and points on the said lines that are close to the said projection $\hat{x}$. If $\hat{x}$ is above $L_2^{cr}$ or below $L_{-2}^{cr}$, then in the case of the improved algorithm use equations (21), (22) and FIG. 16 to find the filtering lines close to the said projection $\hat{x}$. This will give a few values of $\Psi_m(s_0,\beta_j)$ for $\beta_j$ close to $\beta(s_0, x)$.
  Step 55. With interpolation estimate the value of $\Psi_m(s_0, \beta(s_0, x))$ from the said values of $\Psi_m(s_0,\beta_j)$ for $\beta_j$ close to $\beta(s_0,x)$.
  Step 56. Compute the contribution from the said filtered CB data to the image being reconstructed at the point x by multiplying $\Psi_m(s_0, \beta(s_0, x))$ by $-c_m(s,\beta(s_0, x))/[4\pi_2|x-y(s_0)|]$. The appropriate backprojection coefficient $c_m$ is selected using FIGS. 11, 13, and the right panel of FIG. 14 (see also FIG. 15 for the summary). If $\hat{x}$ is above $L_2^{cr}$ or below $L_{-2}^{cr}$, then in the case of the improved algorithm use FIG. 17 to find the appropriate backprojection coefficient $c_m$.
  Step 57. Add the said contributions to the image being reconstructed at the point x according to a pre-selected scheme (for example, the Trapezoidal scheme) for approximate evaluation of the integral in equation (18).
  Step 58. Go to Step 51 and choose a different reconstruction point x. If all reconstruction points x have been processed, go to Step 59.
  Step 59. Go to Step 10 and load the next CB projection into computer memory.

The image can be displayed at all reconstruction points x for which the image reconstruction process has been completed (that is, all the subsequent CB projections are not needed for reconstructing the image at those points). Discard from the computer memory all the CB projections that are not needed for image reconstruction at points where the image reconstruction process has not completed. The algorithm concludes when the scan is finished or the image reconstruction process has completed at all the required points.

For example, if the detector does not provide all the data which is required for the 3PI algorithm, one can employ various techniques for estimating the missing data. In this case by the detector (respectively, cone beam projection) we mean the virtual detector (respectively, virtual cone beam projection), which includes both measured and estimated data. If one is able to estimate the missing data exactly, then the 3PI algorithm will produce exact reconstruction. In this sense we still talk about exact reconstruction under real circumstances, when missing data are found approximately.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of reconstructing images from data provided by at least one detector, comprising the steps of:
   scanning an object in the spiral fashion with at least one detector that detects at least one cone beam projection, the cone beam projection being wider in the axial direction than projections of four turns of the spiral that are adjacent to a current source position; and
   reconstructing an exact image of the scanned object in an efficient manner with a convolution based FBP (Filtered Back Projection) algorithm.

2. The method of claim 1, wherein the scanning step includes acquiring two-dimensional cone beam (CB) projection data of the object using the detectors.

3. The method of claim 2, further comprising the step of:
   using the detectors substantially similar to those required for a 1PI algorithm.

4. The method of claim 2, wherein the scanning step further includes the step of:
   detecting the cone beam projection being wider in the axial direction as compared to a cone beam projection used in a 1PI algorithm.

5. The method of claim 4, wherein the scanning step further includes the step of:
   detecting the cone beam projection being wider by a factor of at least three times in the axial direction as compared to a cone beam projection used in a 1PI algorithm.

6. The method of claim 1, wherein the object includes: a person.

7. A method of computing exact images derived from spiral computer tomography scan with area detectors, comprising the steps of:
   (a) collecting cone beam (CB) projection data from a detector, which is wider than what is required for a 1PI algorithm; the cone beam covering projections of four turns of the spiral that are adjacent to a current source position;
   (b) identifying families of lines on a plane Π intersecting the cone beam projection;
   (c) preprocessing the CB projection data;
   (d) convolution-filtering said preprocessed CB projection data along said lines;
   (e) back projecting said filtered data to form a precursor of said image; and
   (f) repeating steps a, b, c, d, e, until an exact image of the object is completed.

8. The method of claim 7, wherein the scan includes an x-ray exposure of the object.

9. The method of claim 7, wherein the steps (a)–(f) include:
   a 3PI algorithm.

10. A method of computing images derived from computer tomography scan with detectors, comprising the steps of:
    (a) collecting cone beam (CB) data from a detector during a scan of an object;
    (b) identifying three families of lines on a plane DP(s) intersecting the cone beam, wherein s is value of the parameter describing the scan path and corresponding to the current source position, and the three families of lines include:
    (bi) a first family of lines parallel to $\dot{y}(s)$, where
       $\dot{y}(s)$ is the direction of the scan tangent at the current source position;
    (bii) a second family of lines tangent to $\Gamma_1$ and $\Gamma_{-1}$, where
       $\Gamma_1$ is the projection of the scan turn defined by $s<q<s+2\pi$ onto the plane DP(s);
       $\Gamma_{-1}$ is the projection of the scan turn defined by $s-2\pi<q<s$ onto the plane DP(s);
       q is the parameter along the scan path which describes the point being projected;
    (biii) a third family of lines tangent to $\Gamma_2$ and $\Gamma_{-2}$, where
       $\Gamma_2$ is the projection of the scan turn defined by $s+2\pi<q<s+4\pi$ onto the plane DP(s);
       $\Gamma_{-2}$ is the projection of the scan turn defined by $s-4\pi<q<s-2\pi$ onto the plane DP(s);
    (c) preprocessing and shift invariant filtering said data along said lines of said three families;
    (d) back projecting said filtered data to form a precursor of said image; and
    (e) repeating steps a, b, c, and d until an image of the object is completed.

11. The method of claim 10, wherein the preprocessing includes calculation of the derivative of the CB data with respect to source position.

12. The method of claim 10, wherein the shift invariant filtering includes convolving the said preprocessed data with filter $1/\sin \gamma$.

13. The method of claim 10, wherein back projecting said filtered data from the first family of lines involves multiplying the said filtered data by the coefficient $c_m=2/3$, when the projection of x onto DP(s) is located between $L_2^{cr}$ and $L_{-2}^{cr}$, where
    $L_2^{cr}$ is the line parallel to $\dot{y}(s)$ and tangent to $\Gamma_2$;
    $L_{-2}^{cr}$ is the line parallel to $\dot{y}(s)$ and tangent to $\Gamma_{-2}$.

14. The method of claim 10, wherein back projecting said filtered data from lines in the first family of lines involves multiplying the said filtered data by the coefficient $c_m=1/3$, when the projection of x onto DP(s) is located above $L_2^{cr}$ or below $L_{-2}^{cr}$.

15. The method of claim 10, wherein back projecting said filtered data from a line in the second family of lines involves multiplying the said filtered data by the coefficient $c_m=2/3$, when the projection of x onto DP(s) is located between $\Gamma_1$ and $\Gamma_{-1}$ and the point where the line is tangent to $\Gamma_1 \cup \Gamma_{-1}$ is inside the 1PI parametric interval of x.

16. The method of claim 10, wherein back projecting said filtered data from a line in the second family of lines involves multiplying the said filtered data by the coefficient $c_m=-2/3$, when the projection of x onto DP(s) is located between $\Gamma_1$ and $\Gamma_{-1}$ and the point where the line is tangent to $\Gamma_1 \cup \Gamma_{-1}$ is outside the 1PI parametric interval of x.

17. The method of claim 10, wherein back projecting said filtered data from a line in the third family of lines involves multiplying the said filtered data by the coefficient $c_m = \frac{1}{3}$.

18. A method of computing images derived from computer tomography scan with detectors, comprising the steps of:
   (a) collecting cone beam data from a detector during a scan of an object;
   (b) identifying three families of lines on a plane DP(s) intersecting the cone beam, wherein s is value of a parameter describing the scan path and corresponding to the current source position, and the three families of lines include:
   (bi) a first family of lines parallel to $\dot{y}(s)$, where
      $\dot{y}(s)$ is the direction of the scan tangent at the current source position;
   (bii) a second family of lines tangent to $\Gamma_1$ and $\Gamma_{-1}$, where
      $\Gamma_1$ is the projection of the scan turn defined by $s < q < s + 2\pi$ onto the plane DP(s);
      $\Gamma_{-1}$ is the projection of the scan turn defined by $s - 2\pi < q < s$ onto the plane DP(s);
      q is the parameter along the scan path which describes the point being projected;
   (biii) a third family of lines on the plane DP(s) that have at least three points of intersection $s_1, s_2, s_3$ with $\Gamma_{\pm 1}$ and $\Gamma_{\pm 2}$, where
      $\Gamma_2$ is the projection of the scan turn defined by $s + 2\pi < q < s + 4\pi$ onto the plane DP(s);
      $\Gamma_{-2}$ is the projection of the scan turn defined by $s - 4\pi < q < s - 2\pi$ onto the plane DP(s);
   (c) preprocessing and shift invariant filtering said data along said lines of said three families;
   (d) back projecting said filtered data to form a precursor of said image; and
   (e) repeating steps a, b, c, and d until an image of the object is completed.

19. The method of claim 18, wherein the points of intersection $s_1, s_2, s_3$ are determined according to the following rules:

$$s_1 - s = \psi(s_3 - s_2) \text{ if } s + 2\pi < s_3 < s + 4\pi,$$

$$s_3 - s_2 = \psi(s_1 - s) \text{ if } s - 4\pi < s_3 < s - 2\pi,$$

where $\psi(t)$ is a function with the properties $\psi(0) = 0 \, \psi'(t) > 0$, $t \in R$.

20. The method of claim 18, wherein the preprocessing includes calculation of the derivative of the CB data with respect to source position.

21. The method of claim 18, wherein the shift invariant filtering includes convolving the said preprocessed data with filter $1/\sin \gamma$.

22. The method of claim 18, wherein back projecting said filtered data from lines in the first family of lines involves multiplying the said filtered data by the coefficient $c_m = \frac{2}{3}$, when the projection of x onto DP(s) is located between $L_2^{cr}$ and $L_{-2}^{cr}$.

23. The method of claim 18, wherein back projecting said filtered data from a line in the second family of lines involves multiplying the said filtered data by the coefficient $c_m = \frac{2}{3}$, when the projection of x onto DP(s) is located between $\Gamma_1$ and $\Gamma_{-1}$ and the point where the line is tangent to $\Gamma_1 \cup \Gamma_{-1}$ is inside the 1PI parametric interval of x.

24. The method of claim 18, wherein back projecting said filtered data from a line in the second family of lines involves multiplying the said filtered data by the coefficient $c_m = -\frac{2}{3}$, when the projection of x onto DP(s) is located between $\Gamma_1$ and $\Gamma_{-1}$ and the point where the line is tangent to $\Gamma_1 \cup \Gamma_{-1}$ is outside the 1PI parametric interval of x.

25. The method of claim 18, wherein back projecting said filtered data from lines in the third family of lines involves multiplying the said filtered data by the coefficient $c_m = \frac{2}{3}$, when the projection of x onto DP(s) is located above $L_2^{cr}$ or below $L_{-2}^{cr}$.

* * * * *

UNITED STATES PATENT AND TRADEMARK OFFICE
CERTIFICATE OF CORRECTION

PATENT NO. : 7,010,079 B2  
APPLICATION NO. : 10/728136  
DATED : March 7, 2006  
INVENTOR(S) : Alexander Katsevich Page 1 of 1

It is certified that error appears in the above-identified patent and that said Letters Patent is hereby corrected as shown below:

Col. 1, lines 13-14 should read,

STATEMENT REGARDING FEDERALLY SPONSORED RESEARCH OR DEVELOPMENT

This subject invention was made with government support under the National Science Foundation, federal contract numbers DMS0104033 and DMS9704285. The government has certain rights in this invention.

Signed and Sealed this
Eighth Day of March, 2011

David J. Kappos
*Director of the United States Patent and Trademark Office*